United States Patent [19]
Crandall

[11] Patent Number: 5,625,190
[45] Date of Patent: Apr. 29, 1997

[54] FORWARD PROJECTION ALGORITHM

[75] Inventor: Peter S. Crandall, Oconomowoc, Wis.

[73] Assignee: General Electric Company, Milwaukee, Wis.

[21] Appl. No.: 501,185

[22] Filed: Jul. 11, 1995

[51] Int. Cl.$^6$ ................................................. G01T 1/166
[52] U.S. Cl. ............................. 250/363.03; 250/363.04
[58] Field of Search ........................ 250/363.03, 363.04; 364/413.16, 413.21; 378/901

[56] References Cited

U.S. PATENT DOCUMENTS

| | | |
|---|---|---|
| 5,169,942 | 12/1992 | Johnson et al. . |
| 5,230,831 | 7/1993 | Srivastava . |
| 5,241,181 | 8/1993 | Mertens et al. . |
| 5,264,570 | 11/1993 | Johnson et al. . |
| 5,272,343 | 12/1993 | Stearns . |
| 5,272,344 | 12/1993 | Williams . |
| 5,300,782 | 4/1994 | Johnston et al. . |
| 5,378,893 | 1/1995 | Murray et al. . |
| 5,414,623 | 5/1995 | Lu et al. ............................. 364/413.21 |
| 5,438,602 | 8/1995 | Crawford et al. ........................ 378/4 |

OTHER PUBLICATIONS

"A Fast Projector–Backprojector Pair Modeling the Asymmetric, Spatially Varying Scatter Response Function for Scatter Compensation in SPECT Imaging," E.C. Frey et al., *IEEE Transactions on Nuclear Science*, vol. 40., No. 4, Aug. 1993, 1192–1197.

"Frequency Domain Implementation of the Three–Dimensional Geometric Point Response Correction in SPECT Imaging," G. L. Zeng et al., *IEEE Transactions on Nuclear Science*, vol. 39, No. 5, Oct. 1992, 1444–1453.

*Primary Examiner*—David P. Porta
*Assistant Examiner*—David Vernon Bruce
*Attorney, Agent, or Firm*—John S. Beulick; John H. Pilarski

[57] ABSTRACT

A method for forward projecting data from an image volume to a projection plane is described. In one embodiment, the method includes the steps of rotating the image data by a transaxial angle $\phi$ to align the image data with the projection plane. Then, for every axial angle $\ominus$, and for each $y'_0$ and for each value v in the projection plane:

(a) determining $z'_0 = (v - y'_0 \sin \ominus)/\cos \ominus$ and interpolating in the z' direction for each x', to form the line $I(x', y'_0, z'_0)$; and (b) interpolating $I(x', y'_0, z'_0)$ for each value of u.

11 Claims, 3 Drawing Sheets

1

FORWARD PROJECTION ALGORITHM

FIELD OF THE INVENTION

This invention relates generally to image generation and, more particularly, to a forward projection algorithm for image reconstruction.

BACKGROUND OF THE INVENTION

The forward projection algorithm described he, rein is primarily described in the context of image reconstruction in a positron emission tomography (PET) scanner. The algorithm, however, can be utilized in other image reconstruction modalities which implement forward projection, such as computed tomography (CT). Therefore, the discussion regarding PET image reconstruction describes, by way of example, one of the many modalities in which the present forward projection algorithm may be implemented.

PET scanners are utilized to generate images of, for example, portions of a patient's body. Positron attenuation data and/or annihilation events are utilized in generating such images. Positrons (a positron is the antiparticle of the electron) are emitted by radionuclides that have been prepared using a cyclotron or other device. The radionuclides are employed as radioactive tracers called "radiopharmaceuticals" by incorporating them into substances, such as glucose or carbon dioxide. The radiopharmaceuticals are injected into the patient and become involved in such processes as blood flow, fatty acids, glucose metabolism, and synthesis.

Positrons are emitted as the radionuclides decay. The positrons travel a very short distance before encountering an electron, and when that occurs, the position and electron annihilate emitting two photons directed in nearly opposite directions.

For detecting such events, the PET scanner has a plurality of detectors, such as, for example, a ring of detectors that encircle the patient. The detectors comprise crystals, referred to as scintillators, to convert the energy of each 511 keV photon into a flash of light that is sensed by a photomultiplier tube. Coincidence detection circuits connect to the detectors and record only those photons that are detected simultaneously by two detectors located on opposite sides of the patient. The number of such simultaneous events indicates the number of positron annihilations that occurred along a line joining the two opposing detectors. During a scan, hundreds of millions of events are detected and recorded to indicate the number of annihilation events along lines joining pairs of detectors in the ring. The collected data is used to reconstruct an image. Further details regarding PET scanners are set forth in U.S. Pat. Nos. 5,378,893, 5,272,343, and 5,241,181, all of which are assigned to the present assignee.

During a two dimensional acquisition with a PET scanner, annihilation events are assumed to occur between detector pairs around the ring transaxially. During volumetric (three dimensional) acquisition of annihilation events with a PET scanner, the events are assumed to occur between detector pairs around the ring of detectors transaxially and between rings of detectors axially. Although volumetric acquisitions greatly enhance the number of events detected by the system, the data collection is spacially variant over the axial length. The axial spacial variance occurs because there are events which are detected within the scanner by one detector which cannot be detected by a second detector at non-zero axial angle (the events exit the system through the end of the scanner). This "missing data" greatly complicates volumetric data reconstruction.

The most generally accepted method to overcome the "missing data" problem is to first perform a two dimensional reconstruction, typically by filtered back projection, of the data which can be completely measured by the system. The missing data is then estimated by forward projecting from the initial reconstruction of the measured data. Forward projection refers to the projection of data from image space to projection space. The reconstruction process is then completed by merging the forward projected data with the measured data, and then performing a three dimensional reconstruction of the merged data set.

For example, in a known PET scanner, the image matrix to be forward projected is of the size x=y=256 and z=35. To complete the data set, a total of 13,218,240 forward projections are performed. In conventional implementation, the forward projections are organized as 1,888,320 sets with a run length of 3, 5, 7, 9, or 11 points per set. Performance is adversely affected by these short run lengths (vectors) since the processors cannot take advantage of data pipelining optimizations. As a result, the vector processing efficiency is degraded. To perform such forward projections, it is highly desirable to use high performance processors incorporating optimizations such as data pipelining which are supported by vector libraries.

SUMMARY OF THE INVENTION

These and other objects are attained by an algorithm which, in one embodiment, rotates the, image (x, y, z) by transaxial angle $\phi$ to align the images with the projection plane. The new image coordinates (x', y', z') are then related to the projection plane coordinates (u, v) by:

u=x', and v=y' sin$\Theta$+z' cos$\Theta$, where $\Theta$ is the axial angle.

In addition to the u axis being independent of the z axis, the u axis is aligned to the x' axis. With this alignment, the forward projection is performed along the u axis. Particularly, to perform the forward projection, for each angle $\Theta$, for each $y'_0$ (image space) and for each value v in the projection plane, a value for $z'_0 = ((v - y'_0 \sin\Theta)/\cos(\Theta)$ is determined and interpolated in the z' direction for each x', to form the line I(x', $y'_0$, $z'_0$). The line I(x', $y'_0$, $z'_0$) is then interpolated for each value of u to obtain the forward projected data (=I(x(u), $y_0$, $z_0$)).

The above described forward projection algorithm provides the advantages of performing interpolations and projections along the longest axis of the data sets, which is beneficial when utilizing and optimizing a pipelined processor. For example, in a ;known PET scanner, and utilizing the algorithm described above, the forward projections are organized as 47,040 sets having 281 points per set. Utilizing the data in this way allows greater efficiency with high performance processors which make use of optimizations such as data pipelining. Further, the reduction in the number of sets and making each set as large as possible enables a more efficient use of vector processing library sets.

DETAILED DESCRIPTION OF THE DRAWINGS

Figure 1:
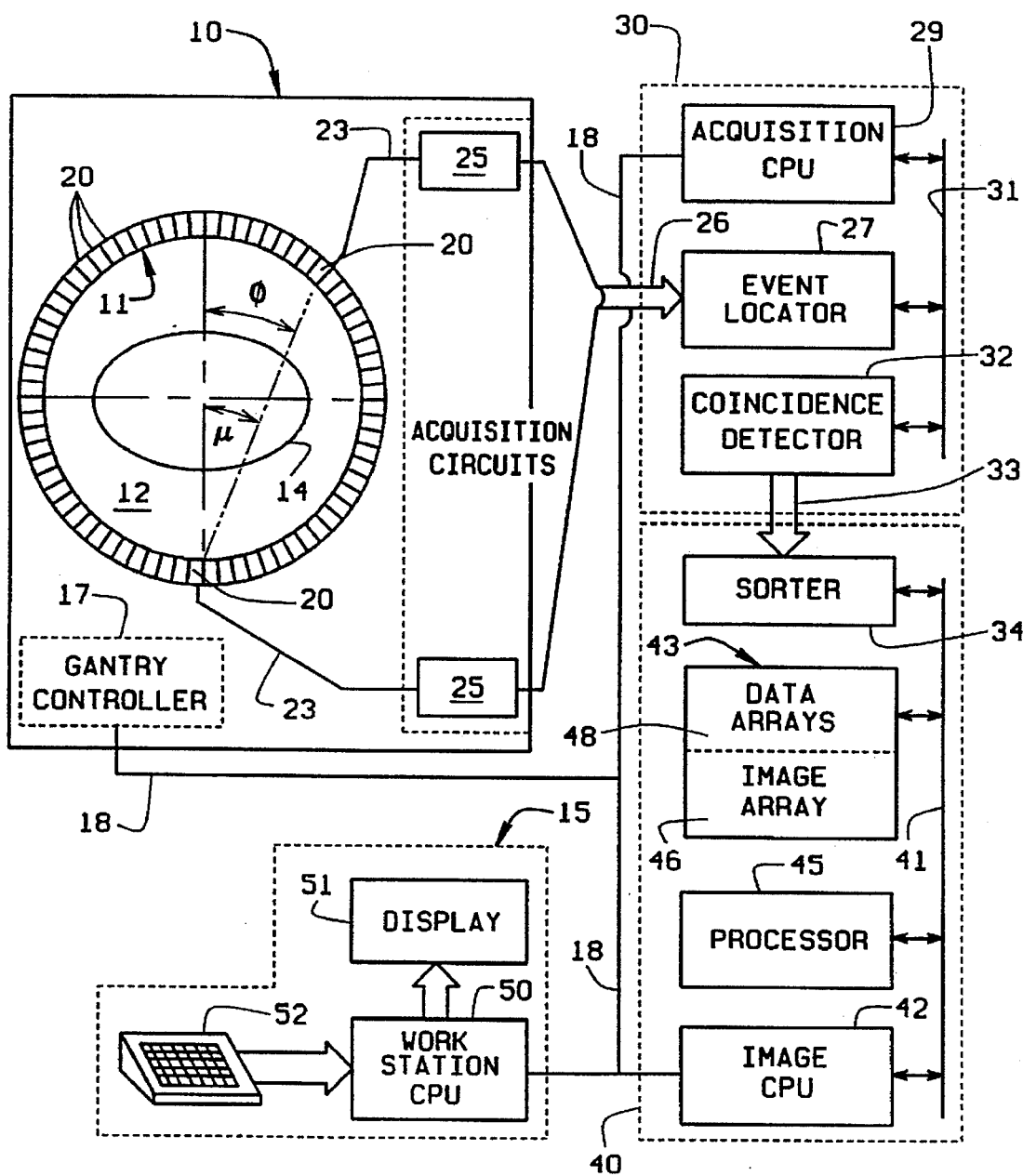
FIG. 1 is a schematic diagram of a PET scanner system.

Referring particularly to FIG. 1, a PET scanner system includes a gantry 10 which supports a detector ring assembly 11 about a central opening, or bore 12. A patient 14 is positioned on a motorized table (not shown) in front of gantry 10 and in alignment with the central axis of bore 12. A table moves patient 14 into bore 12 in response to commands received from an operator work station 15. A gantry controller 17 is mounted within gantry 10 and is responsive to commands received on a serial communications link 18 to operate gantry 10.

Detector ring assembly 11 is comprised of one hundred and twelve radiation detector units 20, for example. Each radiation detector unit 20 includes a set of scintillator crystals arranged in a matrix that is disposed in front of four photomultiplier tubes. Each photomultiplier tube produces an analog signal on line 23 when a scintillation event occurs. A set of acquisition circuits 25 are mounted within gantry 10 to receive these signals and produce digital signals indicating the event coordinates (x, y) and the total energy. The digital signals are transmitted through a cable 26 to an event locator circuit 27 housed in a separate cabinet. Each acquisition circuit 25 also produces an event detection pulse which indicates the exact moment the scintillation event took place.

Event locator circuits 27 form part of a data acquisition processor 30 which periodically samples the signals produced by acquisition circuits 25. Processor 30 has an acquisition CPU 29 that controls communications on a backplane bus 31 and on network 18. Event locator circuits 27 assemble the information regarding each valid event into a set of digital numbers that indicate precisely when the event took place and the position of the scintillator crystal which detected the event. This event data packet is conveyed to a coincidence detector 32 which is also part of data acquisition processor 30.

Coincidence detector 32 accepts the event data packets from event locators 27 and determines if any two of them are in coincidence. Coincidence is determined by a number of factors. First, the time markers in each event data packet must be within 12.5 nanoseconds of each other, and second, the locations indicated by the two event data packets must lie on a straight line which passes through the field of view in the scanner bore 12. Events which cannot be paired are discarded, but coincident event pairs are located and recorded as a coincidence data packet that is conveyed through a serial link 33 to a sorter 34.

Sorter 34 forms part of an image reconstruction processor 40. Sorter 34 counts all events occurring along each projection ray and organizes them into a two dimensional data array 48 which is stored in a memory module 43. The image reconstruction processor 40 also includes an image CPU 42 that controls a backplane bus 41 and links it to local area network 18. A processor 45 also connects to backplane bus 41 and reconstructs images from the data arrays 48. Processor 45 preferably, in one embodiment, is a high performance processor capable of performing data pipelining operations. Processor 45 could be composed of a plurality of coupled processors which perform various assigned tasks. An Intel i860 processor, or an array of Intel i860 processors, for example, can be used for performing such functions. A resulting image array 46 is stored in memory module 43 and is output by image CPU 42 to operator work station 15.

Operator work station 15 includes a CPU 50, a CRT display 51 and a keyboard 52. CPU 50 connects to local area network 18 and scans keyboard 52 for input information. Through keyboard 52 and associated control panel switches, the operator can control the calibration of the PET scanner, its configuration, and the positioning of the patient for a scan. Similarly, the operator can control the display of the resulting image on CRT display 51 and perform image enhancement functions using programs executed by work station CPU 50.

As hereinbefore described, the present invention is specifically directed to a forward projection algorithm which may be utilized in a PET scanner, such as the scanner described above, or in another image reconstruction system such as a CT system. The present forward projection algorithm is not limited to use only in a PET scanner. In addition, the present invention is not directed to an image reconstruction system in its entirety. Rather, the present invention is specifically directed to a forward projection algorithm which may form a part of such a system.

Figure 2:
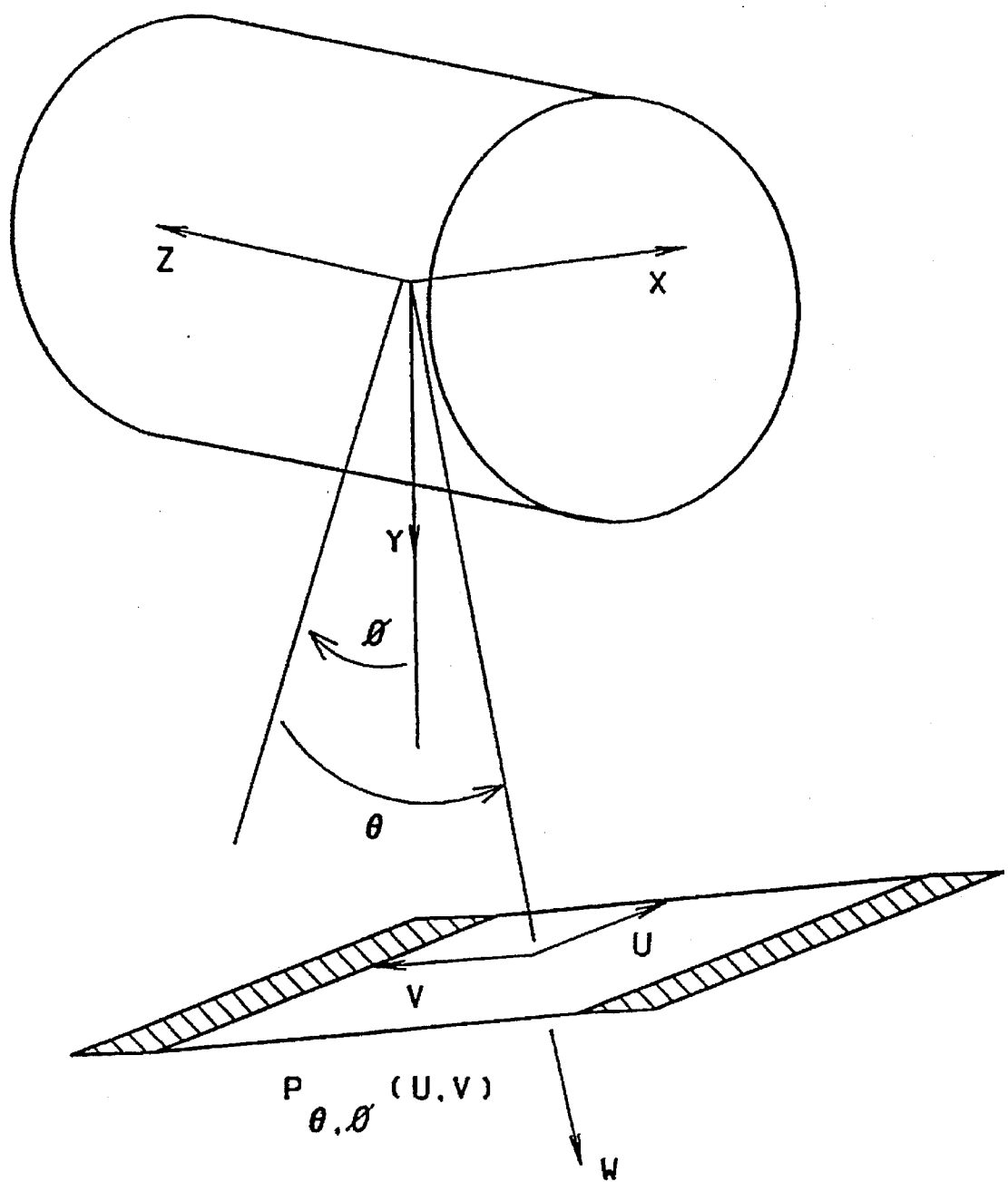
FIG. 2 illustrates volumetric measurements made by a PET scanner.
Figures 1, 3A:
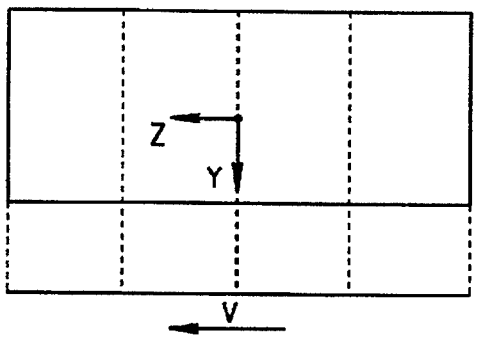
FIGS. 3a(i–ii)–3b(i–ii) illustrate scanner and projection planes for $\Theta$=0 and $\Theta\neq 0$, respectively.
Figures 2, 3A:
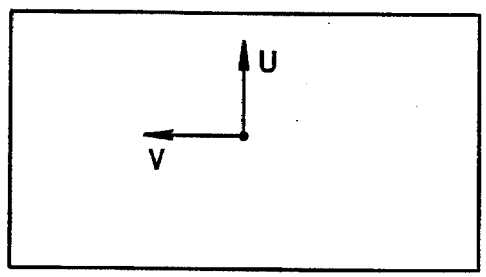
Figures 1, 3B:
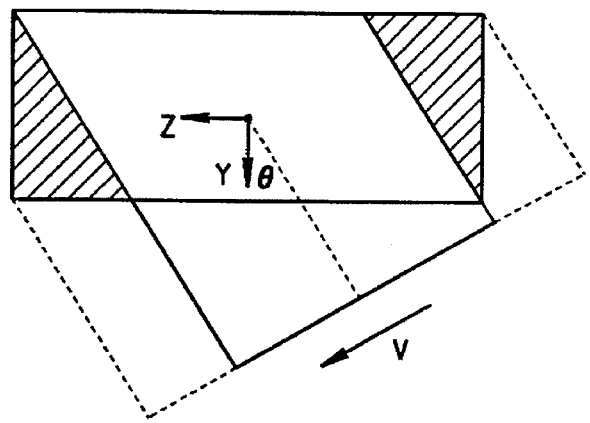
Figures 2, 3B:
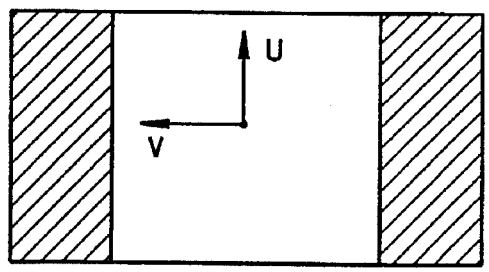

As shown in FIG. 2, and with respect to generating image array 46, the volumetric (three-dimensional) measurement of annihilation events within a PET scanner is accomplished by collecting projection planes $P_{\Theta,\phi}(u,v)$ of the events at each transaxial angle $\phi$ and a set of axial angles $\Theta$. Since the scanner is not spherical or a cylinder of infinite length, not all data cart be measured for angles $\Theta \neq 0$. For example, FIG. 3a(i) is a side view of the scanner and projection plane at an angle $\Theta=0$ and $\phi=0$. FIG. 3a(ii) is a top view of such plane. As shown in FIGS. 3a(i–ii), all data within the scanner bore (the region not hatched) is measured. FIG. 3b(i) illustrates a side view of the scanner and projection plane for an angle $\Theta \neq 0$ and $\phi=0$. FIG. 3b(ii) is a top view of such plane. The hatched regions in FIGS. 3b(i–ii) illustrate the scanner data that could not be measured by the system.

The missing data, i.e., the data for the hatched regions of FIGS. 3b(i–ii), greatly complicates volumetric data reconstruction. Algorithms which use a Colsher filter to perform filtered backprojection require the data to be completed. The most accepted method, known as the reprojection algorithm, to deal with the problem performs a two dimensional reconstruction (typically by filtered back projection) of the data which can be completely measured by the system. The missing data is then estimated by forward projecting from the initial reconstruction of the data. Forward projection refers to the projection of data from image space to projection space. The reconstruction process is completed by merging the forward projected data with the measured data and then performing a three dimensional reconstruction of the merged data set.

Particularly, for every angle $\Theta$ and every angle $\phi$, the image coordinates (x, y, z) and projection plane coordinates (u, v) are related by:

$u = x \cos\phi + \sin\phi$, and $v = x(-\sin\phi\sin\Theta) + y \cos\phi\sin\Theta + z \cos\Theta$.

To forward project the data, the following prior an algorithm has been used:

If $\sin^2 < 0.5$:

For each $y_0$ (image space):
  For each value of u in the projection plane:
    Compute $x_0 = (u - y_0 \sin\phi)/\cos\phi$ and interpolate in the x direction for each z, to form the line $I(x_0, y_0, z)$.
    Compute $z(v) = (v + x_0 \sin\phi\sin\Theta - y_0 \cos\phi\sin\Theta)/\cos\Theta$ and interpolate $I(x_0, y_0, z)$ to get forward projected data $(= I(x_0, y_0, z(v)))$.

else

For each $x_0$ (image space):
  For each value of u in the projection plane:
    Compute $y_0 = (u - x_0 \cos\phi)/\sin\phi$ and interpolate in the y direction for each z, to form the line $I(X_0, y_0, z)$.
    Compute $z(v) = (v + x_0 \sin\Theta\sin\Theta - y_0 \cos\phi\sin\Theta)/\cos\phi$ and interpolate $I(x_0, y_0, z)$ to get the forward projected data $(= I(x_0, y_0, z(v)))$.

Two problems arise in implementing this prior art algorithm for execution by a high performance processor such as processor 45. First, the interpolations in the x or y directions are performed on vectors along the z axis which is the slowest changing index in image array 46, which may cause page faults in memory accesses. Second, the forward projection is performed along the shortest paths through the projection data, which adversely impacts the efficiency of processor 45.

The present invention, on the other hand, structures the data in such a way to reduce the number of forward projections in a vectorized sense by optimizing the length of the data paths provided to a data pipeline. Such a structure optimizes the use of vector processing library calls. Also, the interpolations are performed along the fastest changing index. Particularly, in accordance with one embodiment of the present algorithm, the image volume (x,y,z) is first rotated by $\phi$ to align it with the projection plane. The new image coordinates (x', y'z') are then related to the projection plane coordinates (u, v) by:

u=x', and v='sin$\ominus$+z'cos$\ominus$.

In addition to u being independent of z, it is now aligned to x'. Using this alignment, the forward projection is performed along the u axis rather than the v axis. Specifically, for every angle $\ominus$:

for each $y'_0$ (aligned/rotated image space):

For each value v in the projection plane:

Compute $z'_0=(v-y'_0 \sin\ominus)/\cos\ominus$ and interpolate in the z' direction for each x', to form the line I(x', $y'_0$, $z'_0$).

Interpolate I(x, $y'_0$, $z'_0$) for each value of u to get forward projected data (=I(x'(u),$y'_0$, $z'_0$)).

To execute the algorithm described above, and with a known scanner, for example, three hundred and thirty six rotations of the images to be forward projected are performed. Image rotation is used in many image processing applications, and such routines are available as highly optimized components in commercially available vector processing libraries such as Mercury Computer System's Scientific Algorithm Library (SAL), Mercury Computer Systems, Inc., Chelmsford, Mass.

As a specific quantitative example, for a known PET scanner, the interpolations and projections are performed along the longest axis of the data sets, i.e., x=256 and u=281. A path length of 281 is sufficiently long to benefit from the use of a pipelined processor. Reducing the number of data sets from 1,888,320 to 47,040 significantly reduces the time required to perform forward projections by reducing the "overhead", or number of calls to a vector library. In addition, increasing the path lengths of such data sets optimizes processor pipelining operations. The time savings gained by such optimizations more than compensates for the time required to rotate the images in the above example.

From the preceding description of several embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for forward projecting data from an image volume to a projection plane, said method comprising the steps of:

rotating the image data by a transaxial angle $\phi$ to align the image data with the projection plane so that the image coordinates (x', y'z') are then related to the projection plane coordinates (u, v) by:

u=x', and v=y' sin$\theta$+z'cos$\theta$, where $\theta$ is the axial angle; and for every angle $\theta$, and for each $y'_0$ and for each value v in the projection plane:

(a) determining $z'_0=(v-y'_0\sin\theta)/\cos\theta$ and interpolating in the z' direction for each x', to form the line I(x', $y'_0$, $z'_0$); and (b) interpolating I(x', $y'_0$, $z'_0$) for each value of u.

2. A method in accordance with claim 1 wherein steps (a) and (b) are performed by a processor utilizing data pipelining.

3. A method in accordance with claim 1 wherein the data to be forward projected is data representative of positron annihilation events.

4. A system for performing forward projection of data from image volume to a projection plane, said system comprising a processor programmed to perform the step of:

rotating the image data by a transaxial angle $\phi$ to align the image data with the projection plane so that the image coordinates (x', y'z') are then related to the projection plane coordinates (u, v) by:

u=x', and v=y'sin $\ominus$+z'cos$\ominus$, where $\ominus$ is the axial angle.

5. A system in accordance with claim 4 wherein said processor is further programmed, for every angle $\ominus$, to perform the steps of:

for each $y'_0$ and for each value v in the projection plane:

(a) determining $z'_{0=(v-y'_0}\sin\ominus)/\cos\ominus$ and interpolating in the z' direction for each x', to form the line I(x', $y'_0$, $z'_0$); and (b) interpolating I(x', $y'_0$, $z'_0$) for each value of u.

6. A system in accordance with claim 4 wherein said processor is a processor utilizing data pipelining.

7. A system in accordance with claim 4 wherein the data to be forward projected is data representative of positron annihilation events.

8. A processor programmed to perform forward projection of data from an image volume to a projection plane by:

rotating the image data by a transaxial angle $\phi$ to align the image data with the projection plane so that the image coordinates (x', y'z') are then related to the projection plane coordinates (u, v) by:

u=x', and v=y'sin$\ominus$+z'cos$\ominus$, where $\ominus$ is the axial angle.

9. A processor in accordance with claim 8 further programmed to perform, for every angle $\ominus$, the steps of:

for each $y'_0$ and for each value v in the projection plane:

(a) determining $z'_0=(v-y'_0\sin\ominus)/\cos\ominus$ and interpolating in the z' direction for each x', to form the line I(x', $y'_0$, $z'_0$); and (b) interpolating I(x', $y'_0$, $z'_0$) for each value of u.

10. A processor in accordance with claim 8 wherein said processor is a processor utilizing data pipelining.

11. A processor in accordance with claim 8 wherein the data to be forward projected is data representative of positron annihilation events.

* * * * *